(12) United States Patent
Zubkov et al.

(10) Patent No.: US 7,508,501 B2
(45) Date of Patent: Mar. 24, 2009

(54) METHOD FOR MEASURING SPECTROSCOPIC PROPERTIES OF BULK PRODUCTS AND DEVICE FOR CARRYING OUT SAID METHOD

(76) Inventors: Vladimir Aleksandrovich Zubkov, ul. Kavalergardskaya, 30-14, St.Petersburg (RU) 193124; Vladimir Andreevich Timofeev, pr. Koroleva, 30-2-9, St.Petersburg (RU) 197371; Aleksandr Valeryevich Shamrai, ul. Ushinskogo, 25-1-94, St.Petersburg (RU) 195267

( * ) Notice: Subject to any disclaimer, the term of this patent is extended or adjusted under 35 U.S.C. 154(b) by 332 days.

(21) Appl. No.: 10/597,075
(22) PCT Filed: Nov. 18, 2004
(86) PCT No.: PCT/RU2004/000474
§ 371 (c)(1), (2), (4) Date: Jul. 11, 2006
(87) PCT Pub. No.: WO2005/068984
PCT Pub. Date: Jul. 28, 2005

(65) Prior Publication Data
US 2007/0153282 A1    Jul. 5, 2007

(30) Foreign Application Priority Data
Jan. 16, 2004    (RU) .............................. 2004102057

(51) Int. Cl.
*G01N 21/00* (2006.01)
*G01J 3/44* (2006.01)

(52) U.S. Cl. .................... 356/73; 356/301; 356/432
(58) Field of Classification Search ............... 356/73, 356/301, 244, 440, 432; 250/339.11, 339.12, 250/339.02, 341, 343
See application file for complete search history.

(56) References Cited

U.S. PATENT DOCUMENTS

| | | | | |
|---|---|---|---|---|
| 4,692,620 A * | 9/1987 | Rosenthal | .................... | 250/343 |
| 4,742,228 A * | 5/1988 | Bischoff | .................. | 250/341.1 |
| 5,092,819 A * | 3/1992 | Schroeder et al. | .............. | 460/7 |
| 5,241,178 A * | 8/1993 | Shields | .................. | 250/339.02 |
| 5,448,069 A * | 9/1995 | Tobler et al. | ........... | 250/339.01 |
| 6,791,683 B2 * | 9/2004 | Sjodin | ........................ | 356/326 |
| 7,113,265 B1 * | 9/2006 | Sarrazin et al. | ............... | 356/73 |

\* cited by examiner

*Primary Examiner*—L. G Lauchman
(74) *Attorney, Agent, or Firm*—Christopher L. Parmelee; Walker & Jocke LPA

(57) ABSTRACT

The method for measuring spectroscopic properties of bulk products comprises portioned supplying of a sample in a measurement zone. In order to fully fill said measurement zone, several portions (at least two) are loaded and alternately placed substantially in different areas of the horizontal section of the measurement zone in such away that the uniformed distribution and the density of the product in the measurement zone are provided. Afterwards, the spectroscopic properties of the sample are recorded in a standstill and the sample is removed from the measurement zone.

17 Claims, 10 Drawing Sheets

METHOD FOR MEASURING SPECTROSCOPIC PROPERTIES OF BULK PRODUCTS AND DEVICE FOR CARRYING OUT SAID METHOD

BACKGROUND OF THE INVENTION

The claimed invention is related to analytical instrumentation, in particular, to spectroscopy, spectroscopic methods and devices for measurement of spectroscopic properties of loose products based on replenishment of a portion of the measured sample in the measurement zone and can be used for qualitative and quantitative analysis, for example, analysis of properties of the whole grain.

Methods of infrared spectroscopy has applications in industry and agriculture, they allow to perform fast testing of product'properties on different stages of production, during transportation and storage. For example, it is a commonly accepted practice to make spectroscopic analysis of grain to determine its properties and constituents such as moisture, protein content etc. immediately after harvesting, before loading grain into a storage silo, after transportation and prior to be used for sowing or for baking.

The main requirements to the results of spectroscopic analysis are their reliability and reproducibility. A particular feature of analysis of loose products is an optical inhomogeneity of the samples by its nature, so during analysis several areas of sample or several portions of the same sample have to be measured and then averaged. Therefore it is crucial for obtaining reliable and reproducible results to have constant and reproducible filling of the measurement zone with loose product from sample to sample.

It is known that there is a method of measurement of spectroscopic properties of loose samples [1, 2], that comprises manual filling of the optical cell with a loose product, placing the cell in the measurement zone, measurement of spectroscopic properties of the product in several areas of the filled cell, the cell being immobile during the measurement and being moved between the measurements using a special scanning device. Scanning may be done either by linear movement [1] or by rotation [2] of the optical cell.

The main shortcoming of this method is a necessity to fill the cell manually, that decreases reproducibility of the filling and the speed of analysis, and also increases cost. It becomes important in case if it is necessary to make express analysis of large amounts of product, for example before loading grain into the storage silo during harvesting. Moreover, results of analysis depend upon how accurately the cell was filled (i.e. on qualification of the operator).

It is known that there'a device for measurement of spectroscopic properties of loose products [1], that comprises an optical cell, a device for movement of the optical cell and a measuring device.

But the known device does not have any means for automatic loading and discharge of the measured sample. A set of cell with fixed path lengths that can't be readjusted is used.

It is known that there is a method and there is a device for measurement of spectroscopic properties of loose products [3]. This method comprises delivery of product in the measurement zone under influence of gravity, stopping the sample in the measurement zone with a shutter placed below the measurement zone, compacting the product by vibration, measurement of spectroscopic properties of the sample in still position and discharge of the sample by opening the shutter.

The device for implementation of this known method includes a channel (pipeline) in which the loose product moves, a measurement zone in which the loose flow has a component along the gravity force, a measuring optical window, an optical unit for spectroscopic measurements, a valve (shutter) placed below the measuring optical window that locks the measurement zone to keep the product in the zone, branch of the additional channel (bypass), located upper than the measurement zone that provides the constant level of the product in the measurement zone and the product flow through the main channel (pipeline), and a drive that produces vibration to make sample dense.

This method and the device for its implementation provide automatic loading and discharge of a sample. Constant and reproducible density of the product in the measurement zone is achieved by the constant level of the product and by compacting the sample before measurement to make it dense by shaking.

The main shortcoming of this method of measurement of spectroscopic properties of the loose samples and the device for its implementation is that the vibrations that are used to create dense product in the measurement zone could lead to disadjustment of the optical unit of the device, that in turn would lead to less reliable and reproducible results of measurements, while various methods for protection of the optical unit from vibration increase the complexity and costs of the device drastically.

The method and the device described in [4] are the closest to the claimed invention by the combination of the essential parameters. The method comprises delivery of the sample to the measurement zone using a device for portioned sampling, that loads a certain amount of portions of the product; the measurement zone implemented as a vertical shaft that is closed in the bottom part during the sample loading and the measurement by a special locking device, then the registration of the spectroscopic properties of the sample in a still position. In this way the sample is in motion or still during the measurement, but the measurement of the spectroscopic properties is made when the sample is still.

The device for implementation of this known method of measurement of spectroscopic properties includes a loading bunker, portioned sampling unit made as a paddle wheel, vertical shaft, spectral properties measurement unit, a locking unit that closes the vertical shaft periodically, and a discharge bunker.

This method and the device for its implementation ensure automatic loading and discharge of the sample, that increase the speed of analysis and guarantees that the results are independent form the qualification of the operator.

But the present method and the device do not provide the constant bulk density of the product in the measurement zone with desired accuracy. The device does not provide means for strict control of the volume of the sample loaded in the measurement zone and significant inhomogeneities of the product bulk density in the measurement zone might be caused, for example, by the sample sticking to the paddles of the loading wheel that is quite probable when the products with high moisture content are measured. Moreover, the possibility to adjust the length of the optical path depending on the spectroscopic properties of the product analysed is missing, that decreases the accuracy and reproducibility of the analysis.

BRIEF SUMMARY OF THE INVENTION

The task of the present invention is to obtain high reliability and reproducibility of the results of spectroscopic measurements with provision of the high homogeneity and constant bulk density of the analysed product in the measurement zone.

The task set is solved using the group of inventions:

1. Using the method of measurement of spectroscopic properties of loose products that comprises the product being delivered to the measurement zone by portions, several portions (at least two) being loaded alternately in the different areas of the horizontal section of measurement zone to provide complete filling to ensure uniform loading and constant bulk density of the product in the measurement zone, and the possibility to change the length of the optical path of the measurement zone during the measurement to adjust this length depending on the optical properties of the analysed sample with subsequent discharge of the sample from the measurement one.

2. Using the method of measurement of spectroscopic properties of loose samples, wherein the length of the optical path of measurement zone is set depending on the value of optical absorption of the analysed sample in the measured spectral range that ensures the optical density of the measured sample being in the range that corresponds to the highest accuracy of measurements.

3. Using the device for measurement of spectroscopic properties of loose products that comprises that comprises a loading bunker, an inlet (receiver) hole, a portioned sampling unit with the means for continuous uniform product loading alternately to the different areas of the horizontal section of the measurement zone, a measurement zone, a measuring unit, a unit for closing the measurement zone, an outlet (discharge) hole and a sample drawer, wherein the means for continuous uniform product loading ensures consequent filling of not less than two portions of equal volume, and the measurement zone being equipped with the means for adjustment of optical path length depending on the sample absorption value in the measured spectral range.

Proposed are the different implementations of the means for continuous uniform product loading alternately to the different areas of the horizontal section of the measurement zone.

Proposed is the implementation of the measurement zone closing unit as a dosing unit that perform portional sample discharge from the measurement zone.

Proposed are the different implementations of certain units.

The essence of the invention is that the proposed combination of the parameters allows achievement of high degree of homogeneity and constant product bulk density in the measurement zone during the measurement of spectroscopic properties of loose products by portioned loading with uniform product distribution over the horizontal section area of the measurement zone allows adjustment of the path length of the measurement zone depending on the optical absorption in the measured spectral range and on the bulk density of the analysed product in the measurement zone, and guarantees high accuracy and reproducibility of the results of measurements.

BRIEF DESCRIPTION OF THE SEVERAL VIEWS OF THE DRAWINGS

The essence of the invention is also explained in the drawings wherein.

DETAILED DESCRIPTION OF THE INVENTION

The disclosed method of measurement of spectroscopic properties of loose samples ensures high homogeneity and constant bulk density of the analyzed sample in the measurement zone thanks to the fact that during the loading the sample is delivered to the measurement zone in portions, filling uniformly the horizontal section of the measurement zone area by consequent filling of different areas. In addition the present method ensures highest accuracy of measurements due to the adjustment of the optical path length of the measurement zone for which the optical density of the analysed product in the measured spectral range is in the defined accuracy range. Moreover the possibility to adjust the optical path length allows to measure a wide range of products with substantially different optical properties.

Figure 1:
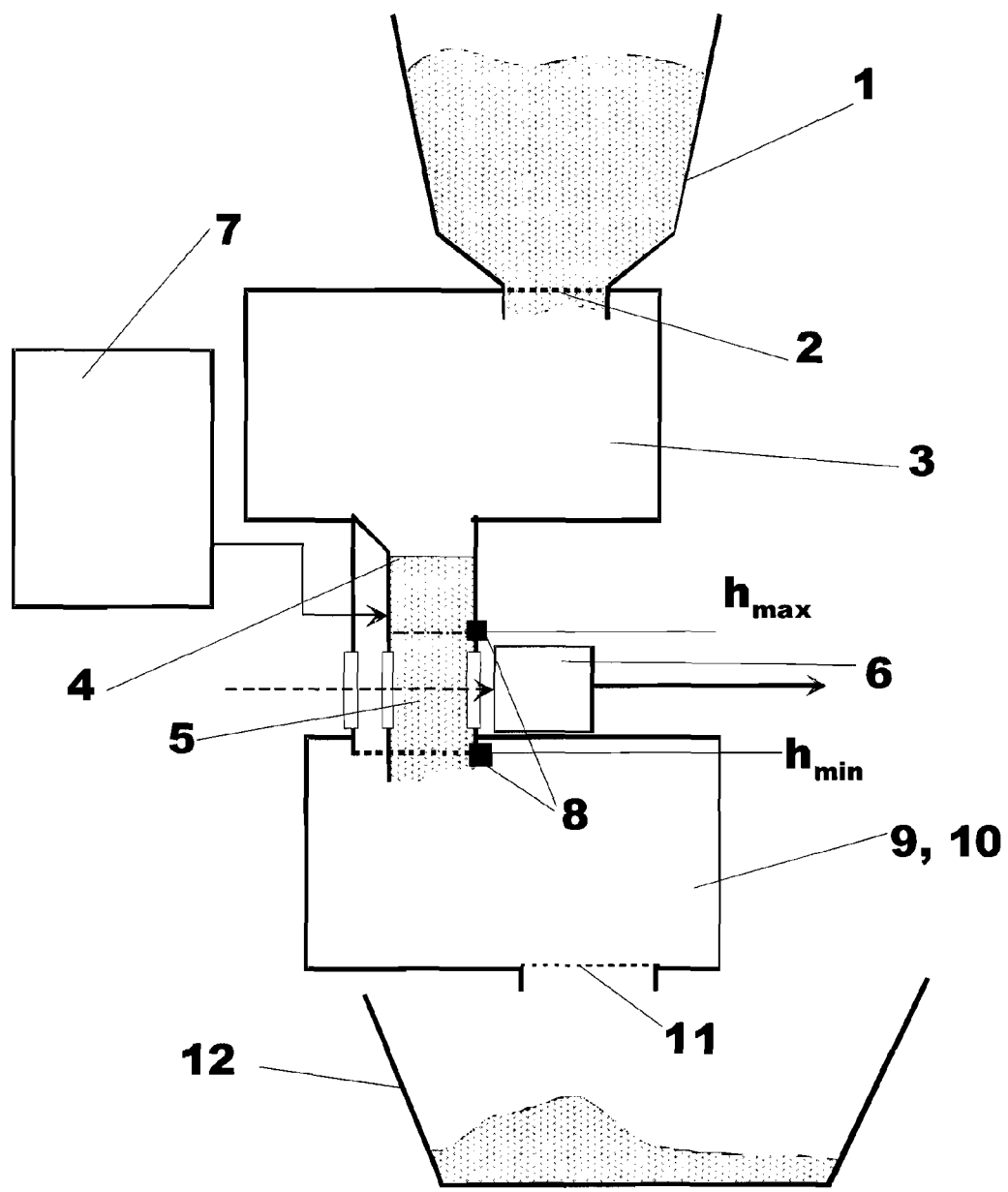
FIG. 1 is a schematic drawing of the claimed device for measurement of spectroscopic properties of loose samples.

The method claimed is implemented in the device for measurement of spectroscopic properties of loose products that comprises the loading bunker 1, connected through the inlet (receiver) hole 2 with the portioned sampling unit 3 (see FIG. 1). The portioned sampling unit is connected with a special channel 4 with the measurement zone located below the portioned sampling unit and made in the form of an optical cell 5 where the measurement of spectroscopic properties is made by the measurement unit 6. Either the optical cell is equipped with a unit for adjustment of the optical path length of the cell 7, or the provision is made to be able to exchange cells with different optical path lengths. The bottom part of the cell 5 is closed by the measurement zone closing unit 9, that stops the movement of the product for the measurement period, and after the measurement the analyzed portion is discharged through the outlet 11 to a special container 12. Provision is made for a device that monitors the level of filling the cell 8, that consist of two optical sensors that indicates the minimal level of the product $h_{min}$, located below the measurement zone 5 and the maximal level $h_{max}$ located above the measurement zone 5.

Figure 2A:
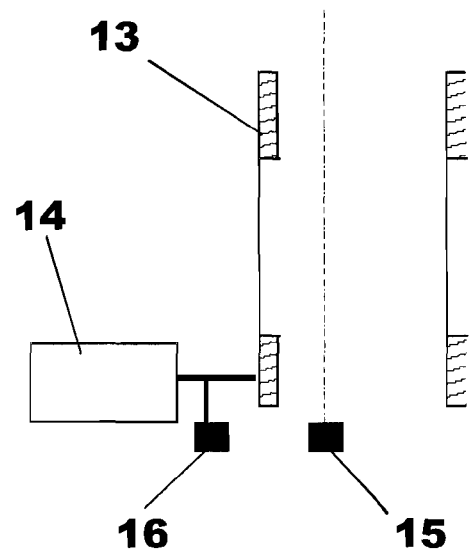
FIG. 2 is a diagram of unit for adjustment of the optical path length of the measurement zone.
Figure 2B:
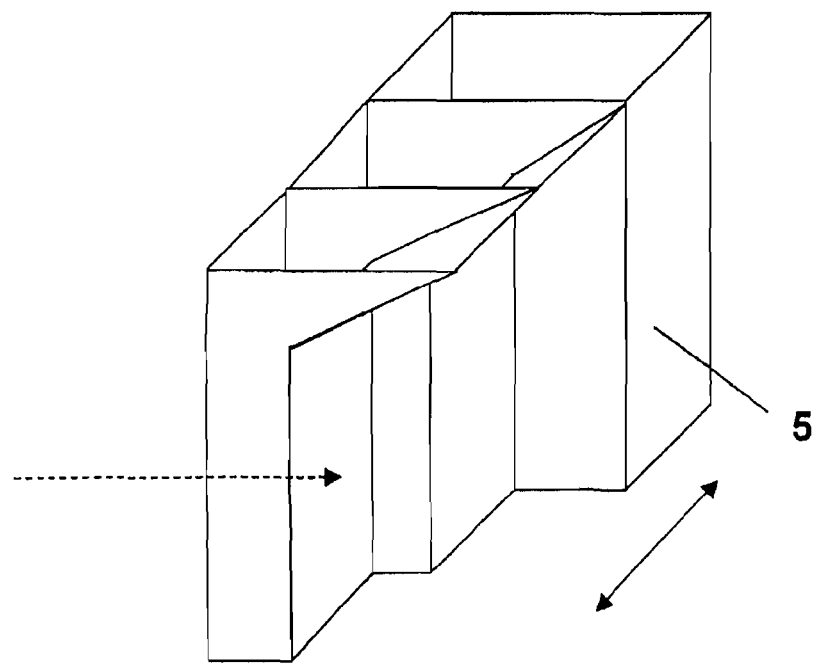

The unit for adjustment of the optical path length 7 (see FIG. 2) consist of a moving wall of the optical cell 13, electromechanic drive 14 and a unit for measurement of optical path length, that includes sensor of initial wall position (minimal length of the cell during the measurements) 15, sensor for measurement of the length of the cell (for example, drive rotation counter) 16. The particular feature of the claimed device is that the portioned sampling unit 3 is equipped with special means for uniform portioned sampling of the product into the measurement zone 5. These means ensure alternate filling of several portions (at least two portions) of equal volume to the different areas of the horizontal section of the measurement zone. Besides the reliability of measurements is substantially increased by the possibility to adjust the length of the optical path length depending on the optical properties of the analyzed sample. Depending on the optical absorption of the analyzed product in the measured spectral range the length of the measurement zone 5 is selected so as the optical density of the sample would fall in a preset range of allowed values for which the use of the dynamic range of the measurement unit 6 is optimal and that for which the signal/noise ration is highest, that guarantee accuracy and reproducibility of measurement result. In addition the level of filling indication unit 8 and the measurement zone closing unit in the form of a dosing unit 10 potentially allow very precise automatic control of the volume of the analyzed product when the portioned sampling unit and the dosing unit 10 are synchronized, it can be used for adjustment of the optical path length of the cell 5 without discharge of the product from the measurement zone to cut down the time of analysis and decrease the amount of sample required for analysis.

Different implementations of the units of the device are presented further.

Figure 3:
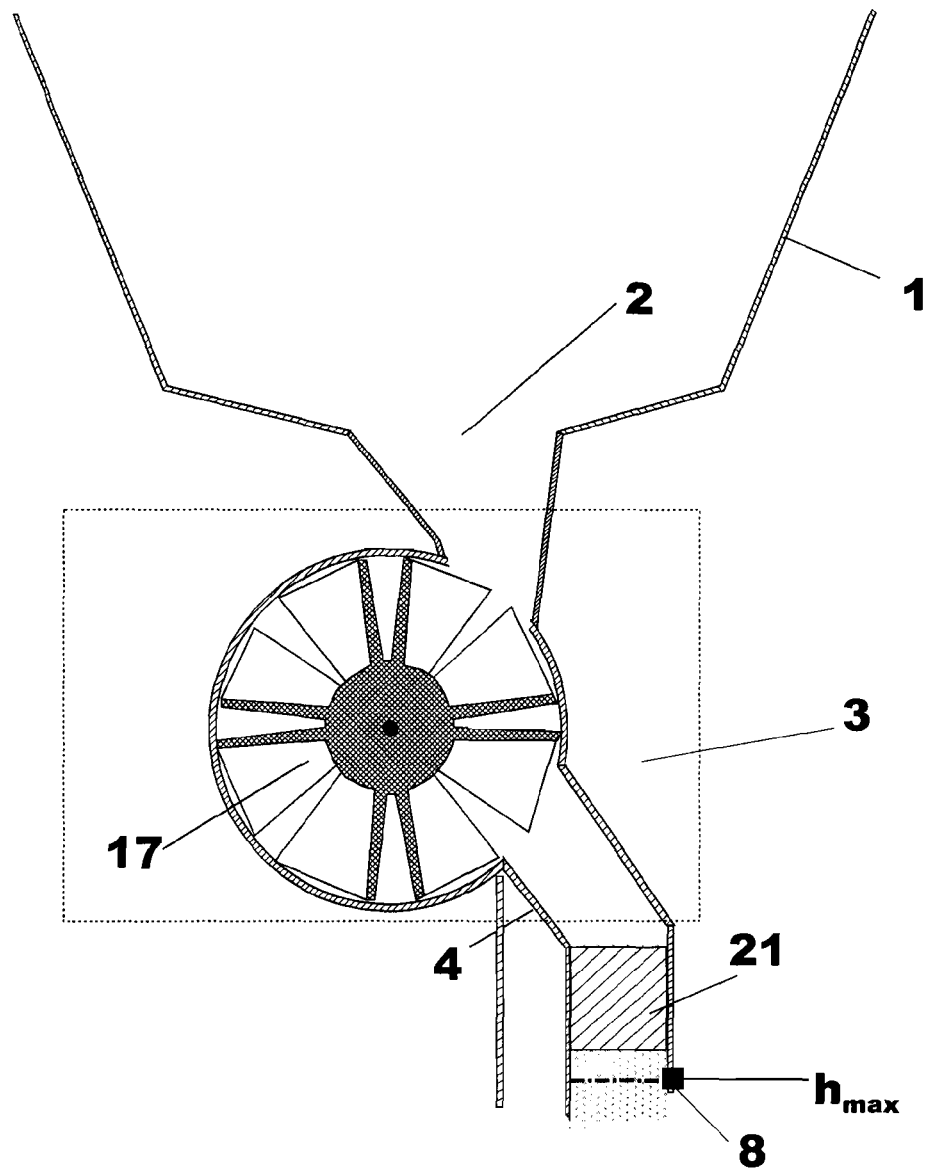
FIG. 3 is one of the implementations of the portioned sampling unit made as a paddle wheel.

The portioned sampling unit can be made in a form of paddle wheel 17, as shown on the FIG. 3. The possible size of particles (grains) of the analysed product should be less than the volume between the two neighbour paddles (for example, larger than corn grain), but at the same time the volume between the paddles should accommodate enough product to fill the optical cell fully with at least two portions, and thus it should not be larger than a half of the minimal volume of the measurement zone (volume of the measurement zone with shortest path length).

Figure 4A:
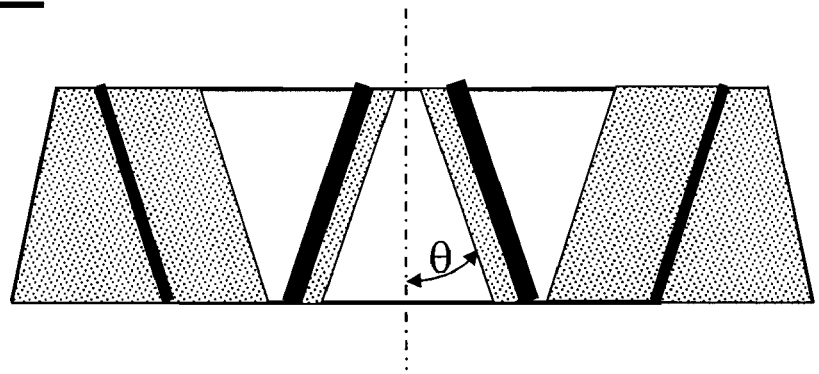
FIGS. 4a-4c show different paddle shapes and the sequence of paddles positions on the wheel.
Figure 4B:
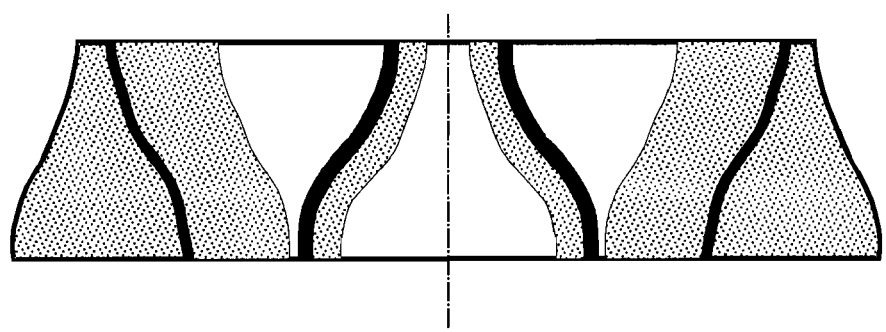
Figure 4C:
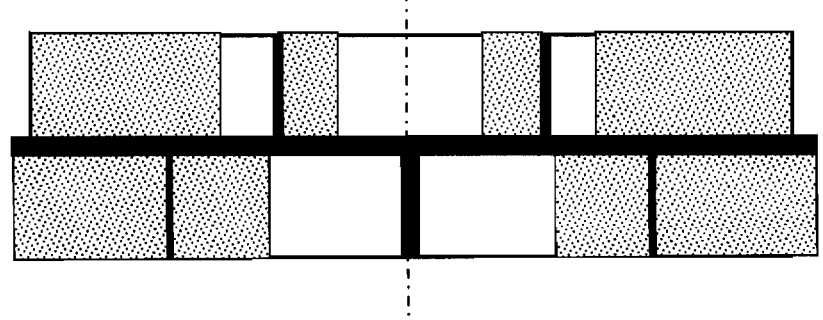

The paddles alternately inclined with respect to the plane perpendicular to the wheel axis are used as the means for consequent uniform sample loading alternately to the different areas of the horizontal section of the measurement, the shape of the surface of the paddles is defined by the area of the horizontal section of the measurement zone to which the paddle loads the product. For example, if the paddles are alternately inclined with respect to the plane that is perpendicular to the rotation axis by the angle θ (see FIG. 4), the product is loaded in the different parts of the cell that ensures high uniformity of filling of the cell and constant bulk density of the product in the measurement zone. Some other examples of shapes of the paddles are shown on the FIG. 4. and different sequences of paddles on the wheel. To provide complete filling of the paddle with loose sample and to provide the constant volume of single portions the inlet (receiver) 2 may be shifted aside from the vertical line that goes through the rotation axis of the wheel (FIG. 3), and the direction of rotation is selected in such a way that the paddles of the wheel would move upwards (to the inlet hole).

The outlet hole 11 also can be shifted from the vertical line that goes through the rotation axis of the wheel (FIG. 3), that provides that the product fills the cell with a uniform flow of minimal thickness.

Figure 5:
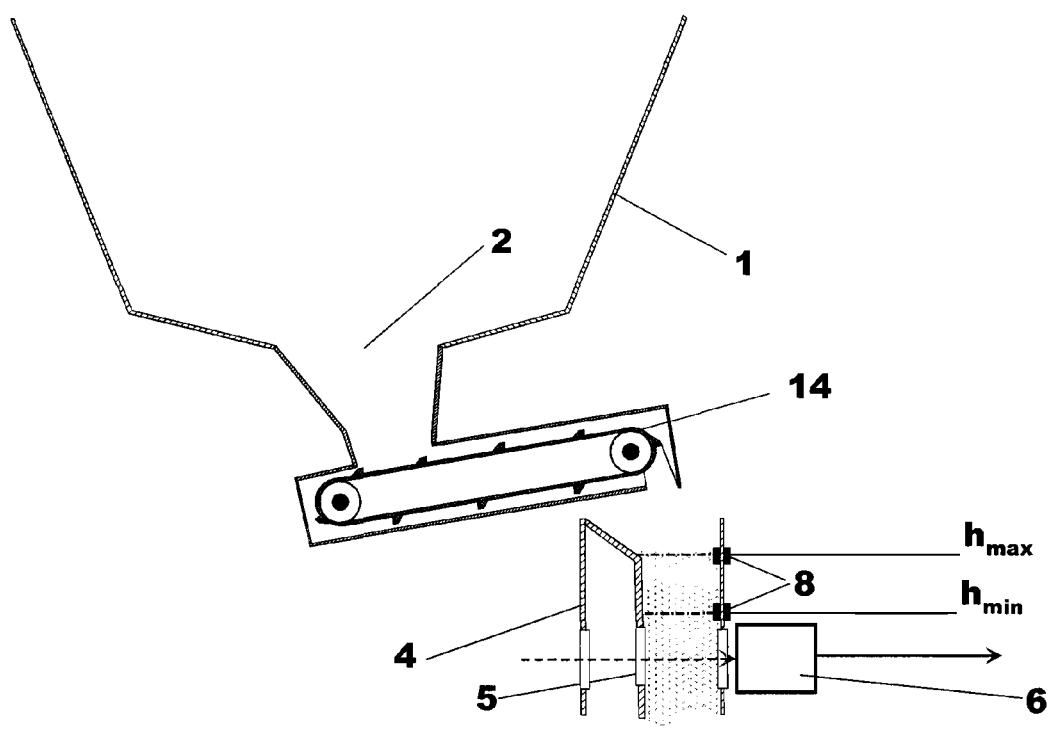
FIG. 5 is a portioned sampling unit made as a conveyer belt.
Figure 6A:
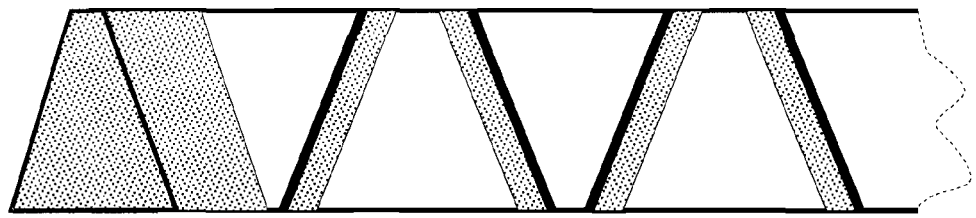
FIGS. 6a-6c show different paddle shapes and the paddle pattern on the belt.
Figure 6B:
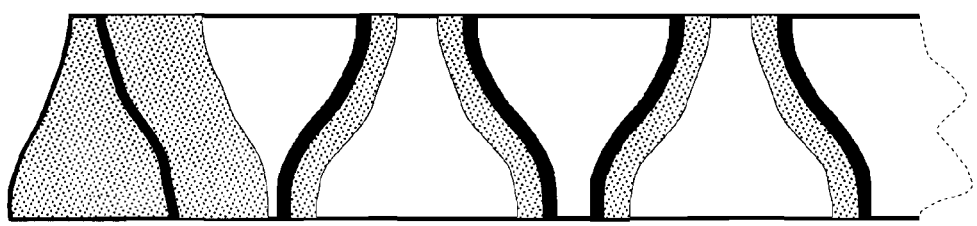
Figure 6C:
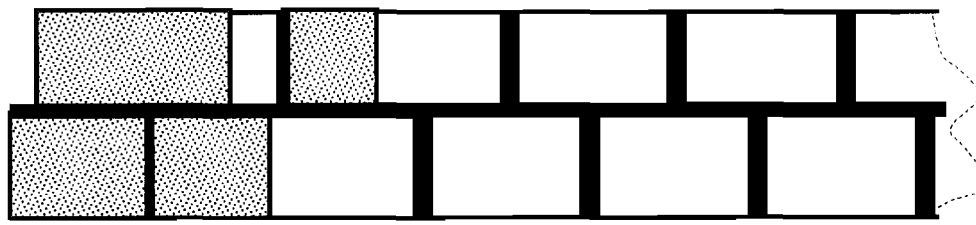

The portioned sampling unit can also be made in a form of a conveyer belt 18, as shown on the FIG. 5, the paddles and the cavities of the belt are made to provide loading of the product by equal portions. The possible size of particles (grains) of the analysed product should be less than the volume of the belt partition (for example, larger than corn), but at the same time this volume should accommodate enough product to fill the optical cell fully with at least two portions, and thus it should not be larger than a half of the minimal volume of the measurement zone (volume of the measurement zone with shortest path length). The paddles of different shapes and placed in different pattern on the belt (FIG. 6) are used as the means for consequent uniform sample loading alternately to the different areas of the horizontal section of the measurement, the shape of the paddles is defined by the area of the horizontal section of the measurement zone to which the paddle loads the product. For example, if the paddles are alternately inclined with respect to the direction of the belt movement under an angle θ (see FIG. 6), the product is loaded in the different parts of the cell that ensures high uniformity of filling of the cell and constant bulk density of the product in the measurement zone. Some examples of the shape of partitions and the patterns on the belt are shown on the FIG. 6.

Figure 7A:
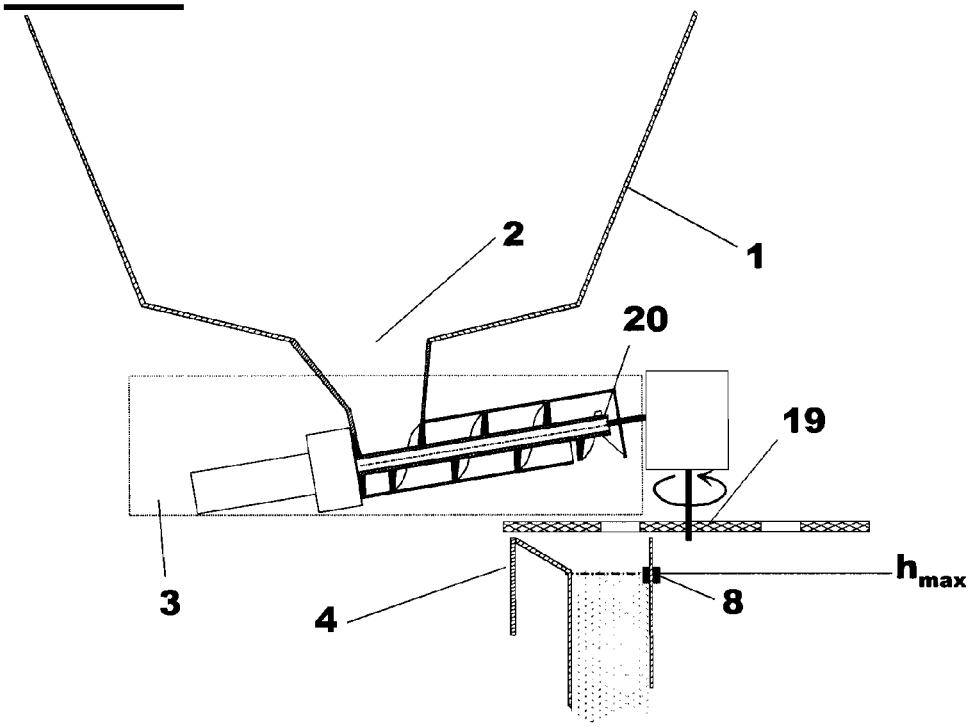
FIGS. 7a-7b show a portioned sampling unit made as a screw feeder with additional device of an automatic shutter of a special shape for uniform sample filling of the horizontal section area of the measurement zone.
Figure 7B:
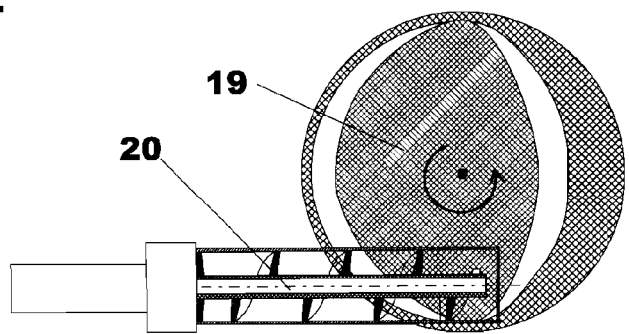

The automatic shutter of a special shape 19 that opens different areas of the horizontal section of the measurement zone may be used as a mean for consequent uniform sample loading alternately to the different areas of the horizontal section of the measurement. One of the examples of implementation of such a shutter in a form of a rotating circle plate with holes made on the different distances from the rotation axis is shown on the FIG. 7. The shutter 19 is synchronised with portioned sampling unit 3. An implementation of the shutter having the same drive as the portioned sampling unit may be done. The portioned sampling unit may be done in a form of a screw feeder 20 if the shutter is used (see FIG. 7).

In addition a baffle can be installed between the portioned sampling unit 3 and the optical cell 5 (see FIG. 3) that would cleave the product flow and thus make the filling of the cell uniformly over the horizontal section of the measurement zone in portions of required volume. The simplest design of the baffle 21 is a plate placed in the channel 4 parallel to the direction of the light beam separating the channel 4 in two sections. When used together with portioned sampling unit 4 in a form of paddle wheel the plate makes the loading of the product in the cell 5 through two different sections of the channel 4 that ensures most dense, uniform and reproducible filling of the cell 5.

Figure 8:
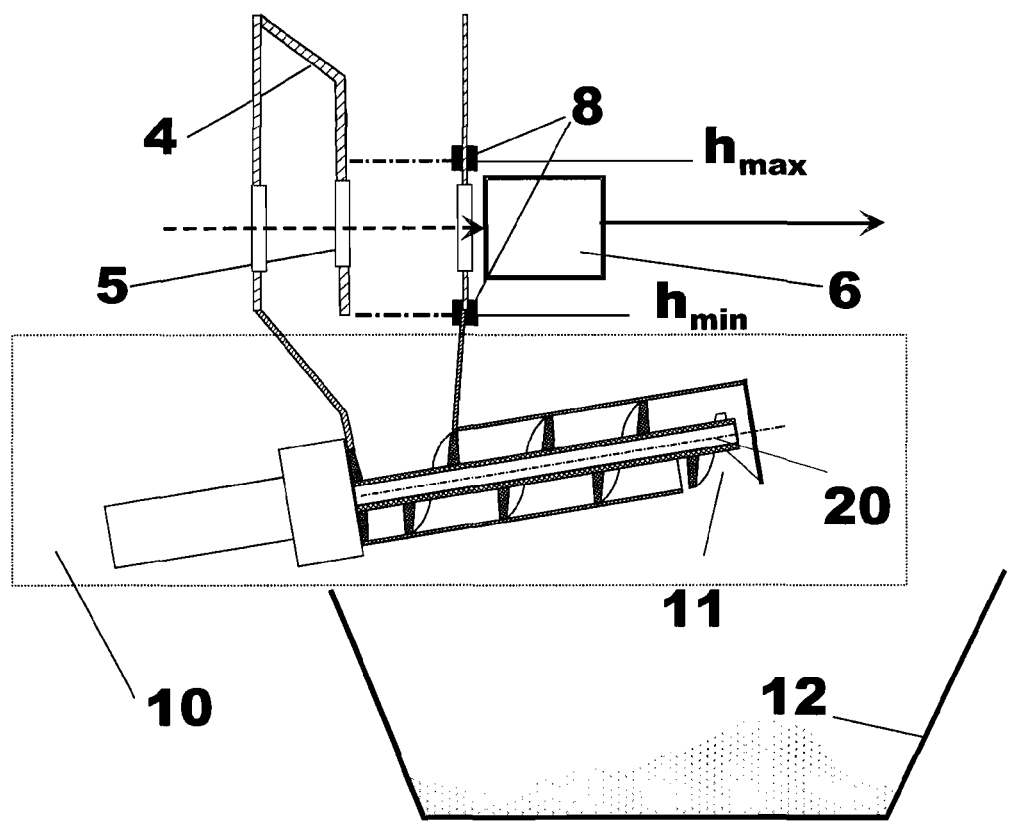
FIG. 8 is a diagram of the measurement zone closing unit made as a screw feeder.
Figure 9:
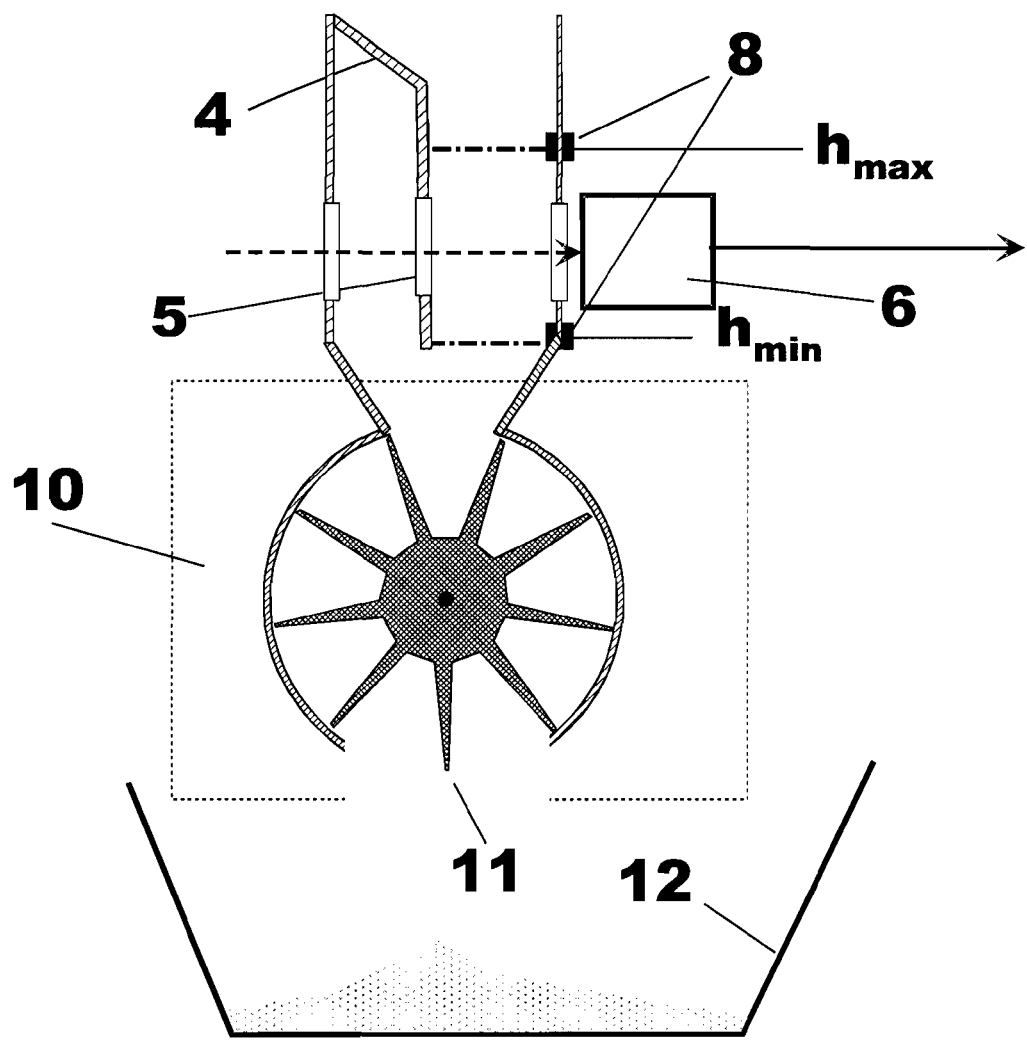
FIG. 9 is a diagram of measurement zone closing unit made as a wheel.
Figure 10:
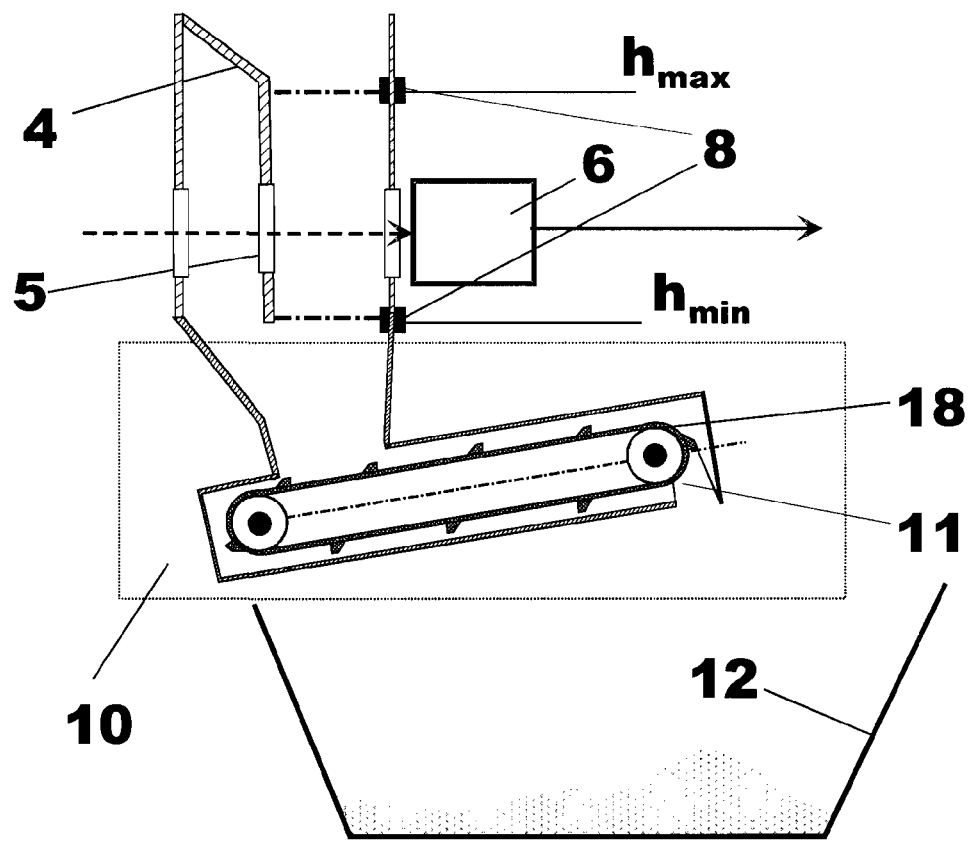
FIG. 10 is a diagram of measurement zone closing unit made as a conveyer belt.

The measurement zone closing unit 9 is required to stop the product flow for the period of measurement of spectroscopic properties and removal of the sample from the measurement zone. The simplest model of the measurement zone closing unit as an automatic shutter, in this case all the content of the of the measurement zone is discharged when the shutter is opened. The measurement zone closing unit made in a form of a dosing unit 10 allows to make sample discharge in portions and offers the possibility to control the amount of the analysed sample portions with high precision that can be used for adjustment of the optical path length of the cell 5 without discharging the product from the measurement zone, shortens the time of the analysis and minimizes the amount of sample required for analysis. The dosing unit can be implemented in different forms—as a paddle wheel (see FIG. 7), as a screw feeder (see FIG. 6) or as a conveyer belt (see FIG. 8).

This device operates in the following way: the sample of the measured product is loaded in the loading bunker 1. Using the optical path length adjustment unit 7 the required optical path length is set that corresponds to the expected optical absorption in the measured spectral range. The adjustment is made with the electromechanical drive 14 that first set the moving wall of the adjustable cell 13 in the minimal path length position, then the electromechanical drive 14 is switched on to move the wall 13 in the direction of increasing the cell length. When the moving wall passes the initial position the sensor that controls this position triggers and the path length measuring sensor checks the length of the cell. When the required length of the adjustable cell 5 is achieved the electromechanical drive stops and the portioned sampling unit 3 is switched starting the filling of the cell. The cell is filled up to the $h_{max}$ level, the process being controlled by the level indication unit 8 that sends a signal to stop sample loading as soon as the level is achieved.

In case if the measurement zone closing unit is made in a form of a dosing unit 10 that provides portioned sample discharge, it is possible to make precise monitoring of product level in the measurement zone. If the maximal level is passed then the dosing unit 10 is activated automatically and it discharge a certain amount of sample that surpasses the $h_{max}$ limit until the desired limit is reached, i.e. the cell 5 is always loaded with the product to the same level. The filling is made with separate portions of constant volume that is larger than half of the minimal path length of the optical cell (cell volume at minimal optical path length) subsequently into different areas of the horizontal section of the cell 5 that ensures uniform and reproducible filling This algorithm of cell loading 5 and the possibility to introduce the unit for monitoring of filling level of the cell 8 provide homogeneous reproducible filling of the cell and let us avoid changes of the level of the filling of the cell caused by erratic operation of the portioned sampling unit 3, for example, due to sticking of the grain to the walls of the loading bunker. After the cell 5 is filled, the first measurement of the spectroscopic properties of the sample is made using the measurement unit 6. Using the level indication unit 8 together with the dosing unit 10 (made in a form for a portioned discharge) it is possible to make fine adjustment of the optical path length by the level of the signal on the output of the measurement unit 6, selecting the optical density of the sample with higher accuracy allows to benefit of use the wider dynamic measurement range. During the adjustment of the optical path length the level of the product in the cell is kept constant $h_{max}$ by synchronous operation of the portioned sampling unit 3 and dosing unit 10.

For example, if it is necessary to make the optical path length shorter, the dosing unit 10 is switched on simultaneously with the optical path length adjustment unit and discharges the required volume of the product. In case if it is necessary to make the optical path length longer then portioned sampling unit is switched on and the product is replenished until it reaches the $h_{max}$ level. In such a way the device allows readjustment of the optical path length without full discharge of the sample from the measurement zone. After the spectroscopic properties of the first sample of the product are measured and the optimal optical path length is set, the first sample is discharged from the cell with the dosing unit and the optical path length remains the same during the whole series of measurements of the sample. The level indication unit signals that the first measured sample portion is discharged when the level of the product in the cell becomes lower than $h_{min}$.

After that the second portion of the sample of the measured product is loaded in the cell. The product is loaded up to the $h_{max}$ level. After that the spectroscopic properties of the second sample are measured, then the sample is discharged from the cell until the level becomes lower than $h_{min}$ that ensures that the analysed product sample in the measurement zone is completely refreshed. Then the loading cycle, measurement of spectroscopic properties of the sample and discharge are repeated several times, usually 10-20 times. After the measurement cycle is finished, the product is fully discharged from the device by the operation of the portioned sample loading unit 3 when the measurement zone closing unit 9 is in opened position or when the sample dosing unit 10 operates during a set period of time after the product level becomes lower than $h_{min}$.

The claimed invention ensures high reliability and reproducibility of the results of the measurements thanks to the uniform and reproducible loading of the product in the measurement zone and possibility to adjust the length of the optical path depending on the optical absorption of the product in the measured region. The distinct feature of the claimed invention is that the analysed sample is delivered to the measurement zone in portions of equal volume with consequent loading in the different areas of the horizontal section of the measurement zone that produces more uniform (with constant bulk density) and reproducible filling of the measurement zone. Additional technical solutions of different elements (shape of paddle wheel, displaced inlet and outlet holes, shape of paddles on the conveyer belt, automatic shutter of and the baffle, placed above the measurement zone) provide most uniform reproducible filling of the cell with sample with optimal product bulk density. Moreover, the possibility to adjust the length of the optical path allows to make measurements of a wide range of products with essentially different spectroscopic properties, and fine adjustment of the length makes it possible to analyse products with optical parameters that varies in a in wide range of values.

REFERENCES

1. InfraLUM FT-10 Operation manual, ver. 152.00.00.00.РЭ.
2. InfraAlyzer 2000 Operation manual, MT1-40EN-09.
3. International claim No WO 98/45678, МПК G01N 1/20, 21/35, published on 15 Oct. 1998.
4. International claim No WO 02/086473 A2, МПК G01N 21/85, published on 31 Oct. 2002.

The invention claimed is:

1. A method of measuring spectroscopic properties of loose products comprising:
    periodically delivering a measured sample of the loose products to a measurement zone using a portioned sampling unit, wherein the measurement zone includes a horizontal section, wherein the portioned sampling unit delivers the sample to the measurement zone in portions of substantially equal volume, not less than two portions being used to fill the measurement zone, including substantially alternately putting the portions in different areas of the horizontal section of the measurement zone so as to provide substantially uniform filling and substantially constant bulk density of the sample within the measurement zone;
    registering spectroscopic properties of the sample in stand-still across the different areas of the horizontal section and;
    removing the sample from the measurement zone.

2. The method of claim 1, wherein registration of the spectroscopic properties of the sample is carried out at a provisional length of an optical length of the measurement zone, said length is set depending on a value of optical absorption of the sample in a measured spectral range, ensuring that a value of an optical density of the sample would be in a range for highest precision of a measurement of the sample.

3. A device for measurement of spectroscopic properties of loose products comprising:
    an inlet,
    a portioned sampling unit, wherein the portioned sampling unit receives products through the inlet,
    a measurement zone positioned below the portioned sampling unit,
    a measuring unit,
    a measurement zone closing unit,
    an outlet through which products are discharged from the measurement zone,
    wherein the measurement zone includes a horizontal section with different areas,
    wherein the portioned sampling unit includes means for uniform portioned sampling of the product into the measurement zone, which means is operative to substantially alternately load portions of the products to the different areas of the horizontal section of the measurement zone, and which means ensures filling of the measurement zone with not less than two portions of substantially equal volume of the products
wherein the measuring unit is operative to measure spectroscopic properties of the products across the different areas of the horizontal section.

4. The device of claim 3, wherein the portioned sampling unit is made as a paddle wheel, wherein the means for uniform portioned sampling of the product into the measurement zone are made as paddles alternately inclined with respect to a plane perpendicular to an axis of the paddle wheel, wherein the paddles each have a shape corresponding to an area of the respective horizontal section of the measurement zone to which the respective paddle loads a portion of the product.

5. The device of the claim 3, wherein the portioned sampling unit is made in a form of a conveyor belt, wherein the means for uniform portioned sampling of the product into the measurement zone are made as paddles alternately inclined with respect to a direction of the belt movement, wherein the paddles each have a shape corresponding to an area of the respective horizontal section of the measurement zone to which the respective paddle loads a portion of the product.

6. The device of the claim 3, wherein the means for uniform portioned sampling of the product into the measurement zone includes a plate placed between the portioned sampling unit and the measurement zone parallel to a light beam direction of the measuring unit and splitting a channel that connects the portioned sampling unit with measurement zone.

7. The device of the claim 3, wherein the means for uniform portioned sampling of the product into the measurement zone includes a shutter made in a form of a rotating wheel with holes therethrough located at different distances from an axis of rotation of the rotating wheel.

8. The device of the claim 7, wherein the shutter and the portioned sampling unit are driven by a common drive, wherein the portioned sampling unit is made in a form of a screw feeder.

9. The device of claim 3 wherein the measurement zone is equipped with a means for measurement of an optical path length of the measurement zone depending on spectroscopic properties and bulk density of the products in the measurement zone.

10. The device of claim 9, wherein the means for measurement of the optical path length of the measurement zone are made in a form of a moving front wall of the measurement zone that moves responsive to a moving wall drive unit and an optical length control sensor.

11. The device of the claim 9 wherein the means for measurement of the optical path length of the measurement zone are made in a form of a set of exchangeable optical cells with different optical lengths, the optical lengths closely coupled with the portioned sampling unit from an upper side and with the unit for closing the measurement zone from the bottom side.

12. The device of claim 3, wherein the inlet and the outlet are shifted aside with respect to a vertical line that goes through an axis of rotation of the wheel.

13. The device of claim 3, wherein the measurement zone closing unit is made in a form of a dosing device that allows portioned discharge of the product from the measurement zone.

14. The device of claim 13, wherein said dosing device is made in a form of a paddle wheel.

15. The device of claim 13 wherein said dosing device is made in a form of a screw feeder.

16. The device of claim 13, wherein said dosing device is made in a form of a conveyor belt.

17. A device for measurement of spectroscopic properties of loose products comprising:
   a portioned sampling unit;
   a measurement zone, wherein the measurement zone includes a horizontal section with different areas, wherein the portioned sampling unit is adapted to carry out uniform product loading substantially alternately to the different areas of the horizontal section of the measurement zone, that ensures filling of the measurement zone with at least two portions of substantially equal volume of the products; and
   a measuring unit, wherein the measuring unit is operative to measure spectroscopic properties of the products across the different areas of the horizontal section.

* * * * *